United States Patent
Barajas et al.

[11] Patent Number: 6,167,291
[45] Date of Patent: Dec. 26, 2000

[54] PROTECTED PIN CONNECTOR FOR AN ELECTROPHYSIOLOGY CATHETER

[75] Inventors: Victor J. Barajas, San Jose; Duane Dickens, San Clemente, both of Calif.

[73] Assignee: Cardima, Inc., Fremont, Calif.

[21] Appl. No.: 09/042,179

[22] Filed: Mar. 12, 1998

[51] Int. Cl.[7] .................................................. A61B 5/04
[52] U.S. Cl. ......................... 600/374; 606/41; 607/122; 439/909
[58] Field of Search ............................. 600/374; 606/32, 606/34, 41; 607/122, 115, 116, 36–38, 101; 439/909, 135, 140, 141, 149, 150

[56] References Cited

U.S. PATENT DOCUMENTS

| | | |
|---|---|---|
| 2,082,986 | 6/1937 | Staley . |
| 2,396,901 | 3/1946 | Tiffany ..................... 173/361 |
| 2,506,979 | 5/1950 | Varnum ..................... 173/363 |
| 2,567,727 | 9/1951 | Quackenbush ............ 173/363 |
| 2,755,449 | 7/1956 | Anderson .................... 339/47 |
| 2,885,648 | 5/1959 | King ............................ 339/36 |
| 3,271,725 | 9/1966 | Bloch .......................... 339/42 |
| 3,683,315 | 8/1972 | Kelly .......................... 339/42 |
| 3,839,697 | 10/1974 | Obert ......................... 339/42 |
| 4,080,025 | 3/1978 | Garneir et al. ........... 339/16 R |
| 4,411,491 | 10/1983 | Larkin et al. .......... 350/96.21 |
| 4,632,121 | 12/1986 | Johnson et al. ........... 128/639 |
| 4,808,127 | 2/1989 | Swanic ...................... 439/139 |
| 4,969,834 | 11/1990 | Johnson ..................... 439/141 |
| 5,030,119 | 7/1991 | Lowe ........................ 439/141 |
| 5,167,516 | 12/1992 | Tan et al. .................. 439/141 |
| 5,383,791 | 1/1995 | Hirakui et al. ........... 439/312 |
| 5,405,375 | 4/1995 | Ayers et al. .............. 607/122 |
| 5,423,689 | 6/1995 | Valentino .................. 439/141 |
| 5,518,411 | 5/1996 | Belleci ..................... 439/141 |
| 5,582,180 | 12/1996 | Manset et al. ............ 128/696 |
| 5,584,712 | 12/1996 | Fukushima ................ 439/141 |
| 5,807,392 | 9/1998 | Eggers ........................ 606/31 |
| 5,836,874 | 11/1998 | Swanson et al. .......... 600/374 |
| 5,843,075 | 12/1998 | Taylor ........................ 606/34 |
| 5,860,920 | 1/1999 | McGee et al. ............ 600/374 |

FOREIGN PATENT DOCUMENTS

| | | |
|---|---|---|
| 0 247 956 | 5/1986 | European Pat. Off. . |
| 1371514 | 10/1963 | France . |
| WO 93/21974 | 11/1993 | WIPO . |

OTHER PUBLICATIONS

Photostatic copy of a connector device for a single conductor (A) having an electrode (B) with a nonconducting tip (C) within a retractable sheath (D).

*Primary Examiner*—Linda C. M. Dvorak
*Assistant Examiner*—David M. Ruddy
*Attorney, Agent, or Firm*—Heller Ehrman White & McAuliffe

[57] ABSTRACT

A connection system which has particular advantages in medical devices such as electrophysiology catheters, and which minimizes the potential for unwanted electrical connections. A cable of the invention has a plurality of leads, with each lead terminated by a pin connector having a retractable insulative sheath so that the chance of unwanted electrical connections is minimized when the pin connector is not connected. The metal pin of the pin connector also has a nonconducting tip member to minimize the chance of short circuits.

9 Claims, 3 Drawing Sheets

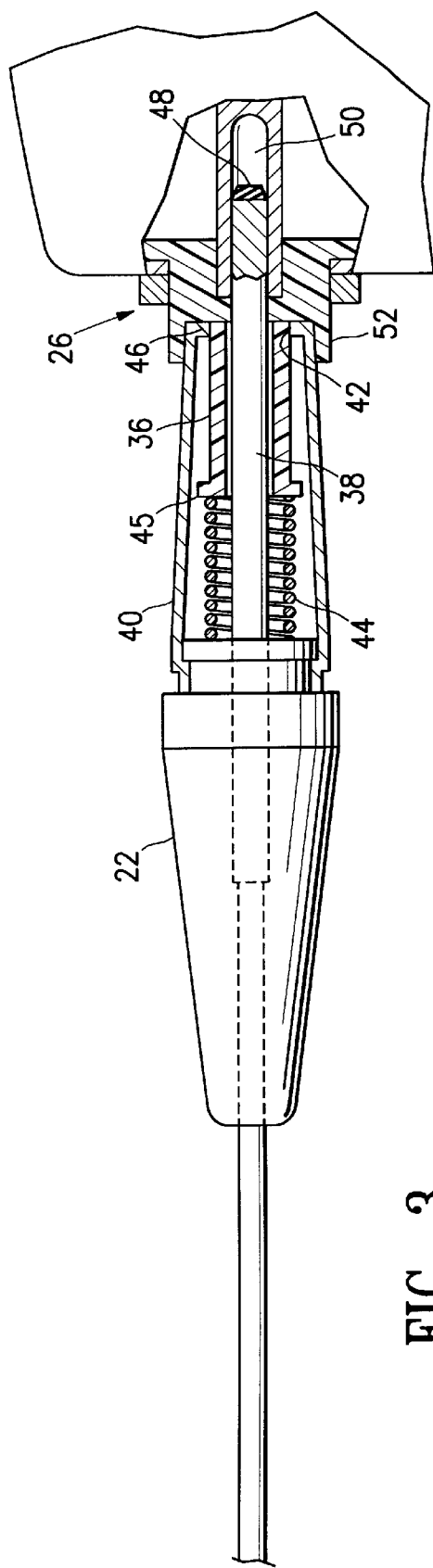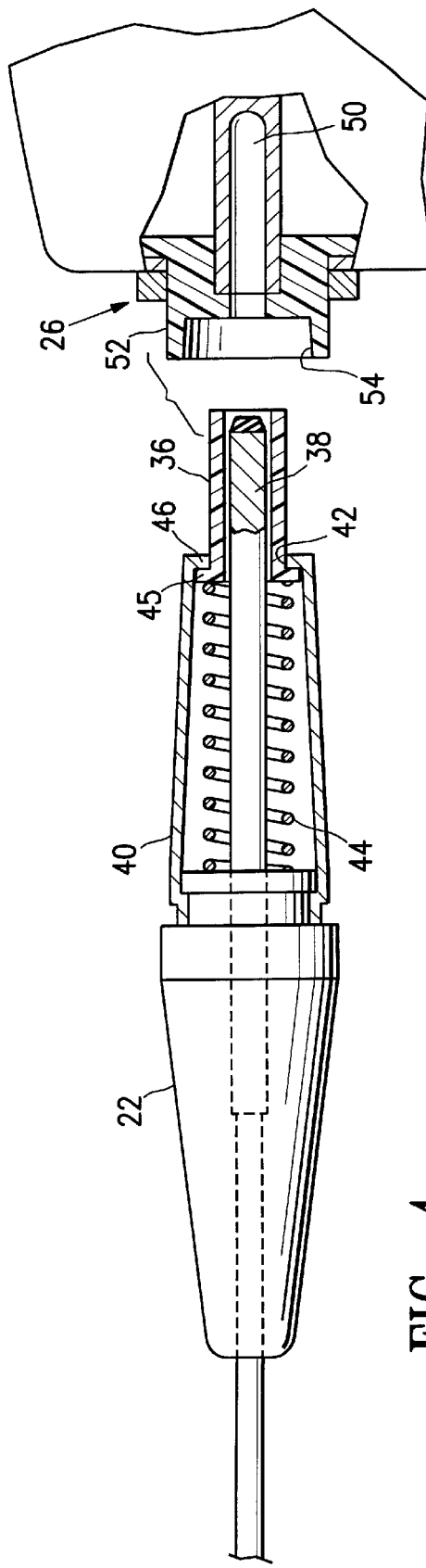

PROTECTED PIN CONNECTOR FOR AN ELECTROPHYSIOLOGY CATHETER

FIELD OF THE INVENTION

This invention relates to the field of electrical connectors for medical devices having electrical leads, and more particularly to an electrophysiology catheter system for conducting energy or collecting signals from living tissue of the patient's body, having an improved connection system to minimize the possibility of creating inadvertent circuits in unconnected leads.

BACKGROUND OF THE INVENTION

Modern electrophysiology ("EP") catheters generally comprise a plurality of precisely spaced electrodes at the distal end of the catheter. Electric potential may be recorded across selected electrode pairs to evaluate the electrophysiologic function of the surrounding tissue. Similarly, electrical impulses may be delivered across selected electrodes to stimulate the surrounding tissue. Additionally, radio frequency ("RF") or other suitable energy may be directed to one or more electrodes to cause ablate malfunctioning heart tissue. RF ablation may be achieved by energizing a single electrode after advancing it to the desired location in the body. In such embodiments, the return electrode comprises an external plate that offers relatively large contact area with the patient's body. This arrangement spreads the return energy over the contact area rather than exiting at one location. Alternatively, two electrodes may be used such that the RF energy is applied between the two electrodes, obviating the need for an external plate.

The electrodes each have a connection to a lead at the proximal end of the catheter which may then be connected in turn to various electronic components to provide the desired function. Further, it is desirable to provide such EP catheters with a connection system so that each electrode may be quickly and individually switched from one functionality to another. Accordingly, an electronic interface, such as a switch box, may be used to allow each lead to be connected with the various types of electronic components, e.g. RF frequency generation, ECG mapping, cardiac pacing and the like, without physically plugging and unplugging the leads.

Prior art EP catheters suffer from certain drawbacks. Specifically, conventional designs for connecting EP catheters to mapping, pacing or ablating equipment make use of a cable with exposed connectors which, consequently, can inadvertently become electrically activated. For example, the exposed connectors may accidentally come into contact with a ground which is typically at some potential other than the patient ground, thereby creating an unwanted electrical circuit. This is of particular concern when dealing with the heart because stray electrical currents can cause fibrillation or undesirable tissue damage. Accordingly, there remains a need for connector systems which minimize the possibility of inadvertent electrical contact while still allowing easy electrical connection. This invention satisfies these and other needs.

SUMMARY OF THE INVENTION

The invention comprises an improved electrical pin connector which is protected from inadvertent or undesirable electrical contact, such as electrical connections in medical devices. The pin connector of the invention is particularly suitable for use in a connection system for an intracorporeal device such as an EP catheter, to thereby minimize the potential for an electrode on the catheter to accidentally become electrically energized.

Generally, the pin connector comprises a conducting pin and a retractable insulative sheath surrounding the pin. The conducting pin preferably has a nonconducting tip member at the free end.

One presently preferred embodiment of the invention comprises a cable having a distal end with a modular plug configured to mate with and provide electrical connections with an EP catheter, and a proximal end having a plurality of leads, each terminated by a pin connector having a retractable insulative sheath. Systems of the invention may comprise the EP catheter and a switch box configured to connect the various electrodes of the catheter to desired therapeutic and diagnostic equipment, such as pacing, recording or ablating components. In preferred embodiments, the retractable insulative sheath comprises a tube that moves coaxially along the metal pin from a first position that covers the metallic surface of the pin and a second position that exposes a portion of the pin. The switch box receptors may be configured to interact with the insulative sheath, causing it to retract to the second position when the pin connector is inserted into the receptor.

The pin connector of the invention having a retractable insulative sheath around the conducting pin minimizes inadvertent electrical connections, yet it provides for quickly and easily engaging or disengaging electrical connections between leads of a EP catheter cable and various electrical components. Preferably, the insulative sheath is biased to extend along the length of the conducting pin and around the non conducting tip member on the free end of the conducting pin, so that no part of the conducting pin is exposed when the pin connector is unconnected. These and other advantages of the invention will become more apparent from the following detailed description and accompanying exemplary drawings.

BRIEF DESCRIPTION OF THE DRAWINGS

FIG. 3 is a detail view, partially in section, showing a single pin connector from the cable, with the insulating sheath retracted, seated in the female receptor of the switch box.

FIG. 4 is a detail view, partially in section, showing a single pin connector from the cable with the insulating sheath extended and the female receptor of the switch box.

DETAILED DESCRIPTION OF THE INVENTION

Figure 1:
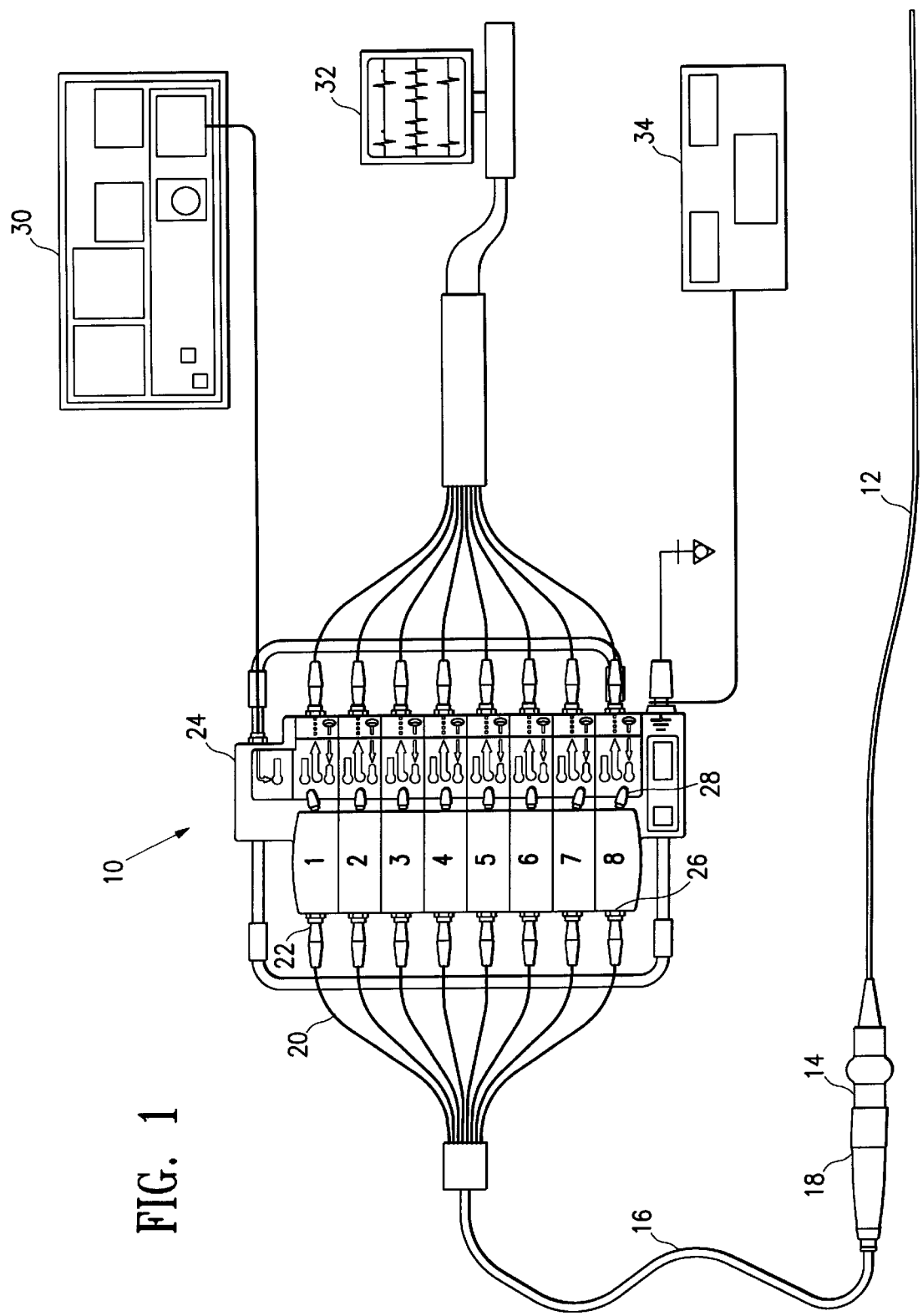
FIG. 1 is a schematic view of the EP catheter system of the invention comprising the cable, the switch box and the various ablating, pacing and mapping equipment.

FIG. 1 schematically illustrates an electrophysiology catheter system 10 embodying features of the invention. Generally, an EP catheter 12 is connected via a modular plug 14 to cable 16. Modular plug 14 provides an electrical connection for each electrode on the distal end of catheter 12 via insulated wires running the length of the catheter shaft. Cable 16 similarly has a modular plug 18 configured to mate with plug 14 and provide a electrical connection with each electrode. The proximal end of cable is divided into a plurality of leads 20 terminated with pin connectors 22 which correspond to each electrode of catheter 12. As shown in FIG. 1, catheter 12 has 8 electrodes and thus the system provides 8 leads 20. However, other common embodiments employ 16 electrodes and a cable having 16 leads. Other numbers of electrodes and leads may also be desirable. A switch box 24 generally comprises a series of receptors 26 configured to receive pin connectors 22. Each receptor 26 connects to a switch 28 that is in turn connected to RF generator 30, ECG mapping equipment 32, and pacing equipment 34. By operation of the switches, each electrode can be connected to the desired componentry. Other suitable equipment may also be employed.

Figure 2:
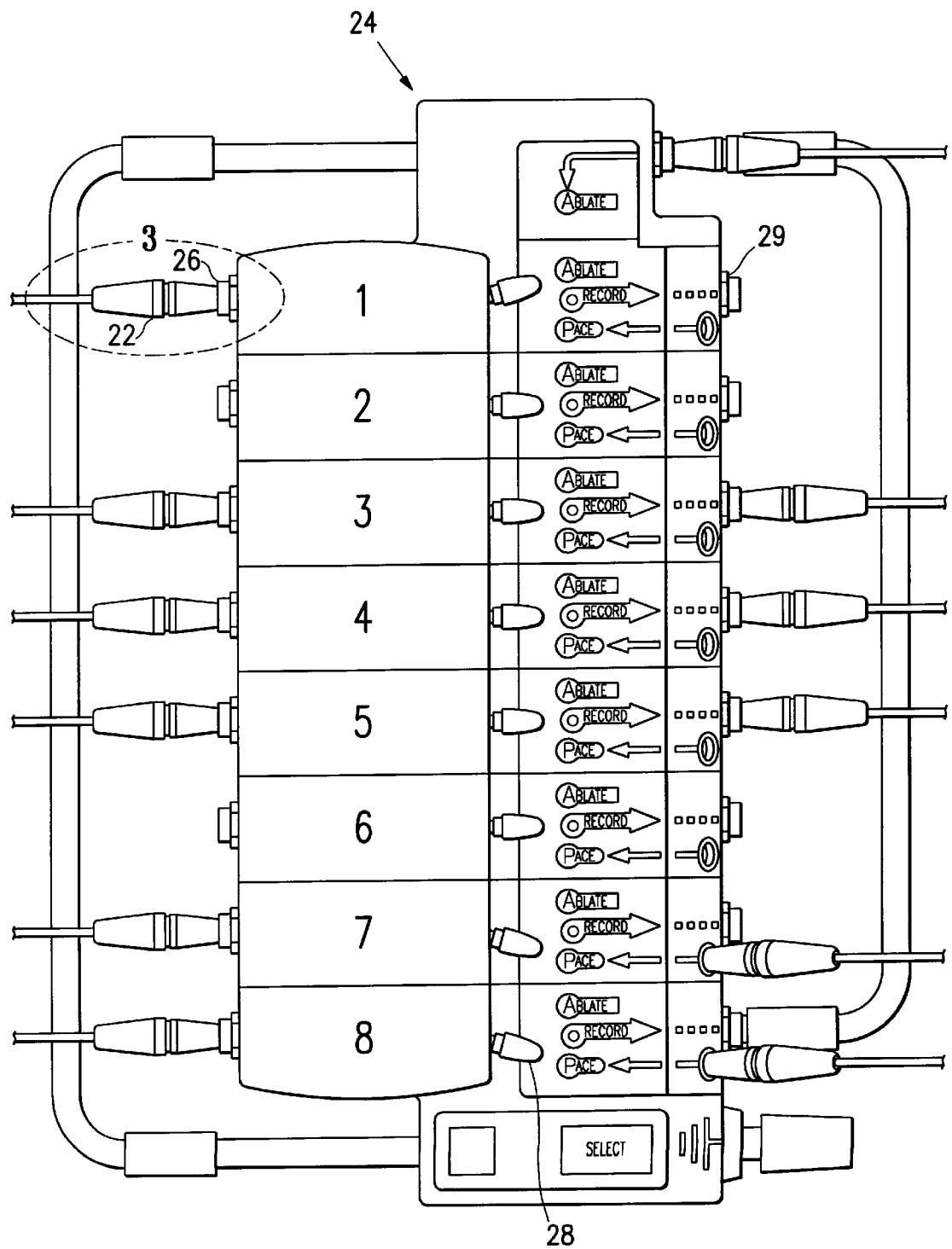
FIG. 2 is a detail view of the switch box showing the connections between the cable pin conductors and the leads from the various pieces of equipment.

A detailed view of switch box 24 is shown in FIG. 2. Again, the pin connectors 22 plug into receptors 26 while switches 28 connect the respective leads 20 to the ablating, recording, or pacing equipment. Switch box 24 also provides the necessary receptors 29 for connection of the electronic componentry.

FIGS. 3 and 4 show detailed views of a pin connector 22 and its complementary receptor 26 in engaged and disengaged positions, respectively. Pin connector 22 has an insulative sheath 36, that may generally comprise a tube coaxially disposed about the metal pin 38 of pin connector 22. Sheath 36 may slide axially to extend or retract along metal pin 38 so as to cover and insulate pin 38 as shown in FIG. 4 or to expose an electrical conductive portion of pin 38 as shown in FIG. 3. Pin connector 22 also comprises a generally cylindrical pin housing 40 having an opening 42 that accommodates retracted insulative sheath 36. Within pin housing 40, spring 44 is disposed coaxially around metal pin 38 and biases insulative sheath 36 in the extended configuration shown in FIG. 4. Insulative sheath 36 has a flange 45 configured to intercept lip 46 on pin housing 40 to restrain sheath 36 in its extended position and prevent it from sliding completely off. Additionally, pin 38 has a nonconducting tip member 48 at the free end to further reduce the possibility of forming an unwanted electrical connection. As shown in FIG. 4, no electrically conductive portion of metal pin 38 is exposed when the insulative sheath 36 is extended. Further, even if the tip of pin connector 22 were accidentally pushed against a conducting surface, only the nonconducting tip member 48 would come into contact with that surface. The nonconducting portions of the system, the sheath 36, the housing 40 and the tip member 48 may be formed from polycarbonate or other suitable materials.

Receptor 26 generally comprises a metallic socket 50 configured to receive and form an electrical connection with pin 38. Receptor 26 also comprises a receptor housing 52 having an opening large enough to accommodate pin 38 but too small to pass insulative sheath 36. Accordingly, as shown in FIG. 3, when pin connector 22 is inserted into receptor 26, sheath 36 is restrained by receptor housing 52 and driven back into pin housing 40, exposing pin 38 to allow an electrical connection with socket 50. Receptor housing 52 may also be configured to have a larger recess 54 designed to accommodate the outer diameter of pin housing 40, to further enhance the mechanical connection between pin connector 22 and receptor 26.

A general description of the device of the present invention as well as a preferred embodiment of the present invention has been set forth above. One skilled in the art will recognize and be able to practice many changes in many aspects of the device described above, including variations that fall within the teachings of this invention. The spirit and scope of the invention should be limited only as set forth in the claims which follow.

What is claimed is:

1. An improved method of performing a medical procedure using an electrophysiology device, which minimizes the potential for an electrode on the device to accidentally become electrically energized, comprising
   a) providing an electrophysiology system comprising
      an elongated electrophysiology device having a proximal end and a distal end, at least one electrode disposed about the distal end of the device;
      a cable with at least one electrical conductor extending through the cable, a distal end having a plug configured to mate with and provide electrical connection to the electrophysiology device, and a proximal end having at least one lead, the at least one lead being terminated by a pin connector having a housing with an opening and a lip, a conducting pin extending from the housing opening, a displaceable insulative sheath in surrounding relation to the conducting pin with a flange configured to intercept the housing lip, and a nonconductive tip member on the conducting pin; and
      an electronic interface having at least one receptor configured to mate with the pin connector;
   b) inserting at least a section of the pin in the receptor and thereby at least in part displacing the sheath so that the pin is in electrically conductive contact with the interface; and
   c) insulating the pin from electrical contact outside of the receptor by biasing the sheath to extend over the pin and a part of the nonconductive tip member which is less than the entire lengh of the nonconductive tip member when the pin and nonconductive tip member thereon are removed from the receptor so that the sheath extends over an electrically conductive portion of the pin when the portion of the pin is outside of the receptor.

2. An improved method of performing an ablation procedure on a patient using an electrophysiology device, which minimizes the potential for an electrode on the device to accidentally become electrically energized, comprising
   a) providing an electrophysiology system comprising
      an elongated electrophysiology device having a proximal end and a distal end, at least one electrode disposed about the distal end of the device, and a modular plug at the proximal end of the device having an electrical connection with the at least one electrode;
      a cable with at least one electrical conductor extending through the cable, a distal end having a modular plug configured to mate with and provide electrical connection to the electrophysiology device, and a proximal end having at least one lead, the at least one lead being terminated by a pin connector having a housing with an opening and a lip, a conducting pin, a displaceable insulative sheath in surrounding relation to the conducting pin with a flange configured to intercept the housing lip, and a nonconductive tip member on the conducting pin, the pin connector being configured to be connected to a high frequency electrical energy source; and
      an electronic interface having at least one receptor configured to mate with the pin connector;
   b) inserting at least a section of the pin in the receptor and thereby at least in part displacing the sheath so that the pin is in electrically conductive contact with the interface;

c) electrically energizing at least one electrode on the device with high frequency electrical energy to ablate the patient's tissue; and d) insulating the pin from electrical contact outside of the receptor by biasing the sheath to extend over the pin and a part of the nonconductive tip member which is less than the entire length of the nonconductive tip member when the pin and nonconductive tip member thereon are removed from the receptor so that the sheath extends over an electrically conductive portion of the pin when the portion of the pin is outside of the receptor.

3. An electrophysiology system, comprising a) an elongated electrophysiology device having a proximal end and a distal end, and at least one electrode disposed about the distal end of the device; and b) a cable with at least one electrical conductor extending through the cable, a distal end having a plug configured to mate with and provide electrical connection to the electrophysiology device, and a proximal end having at least one lead, the at least one lead being terminated by a pin connector having a housing with an opening and a lip, a pin extending from the housing opening, a retractable insulative sheath in surrounding relation to the pin with a flange configured to intercept the housing lip, and a nonconducting tip protector on a free end of the pin, the retractable insulative sheath being moveable from a first position that covers the pin and a part of the nonconducting tip protector which is less than the entire length of the nonconducting tip protector to a second position that exposes at leas a portion of the pin.

4. The electrophysiology catheter system of claim 3 having a plurality of electrodes disposed about the device, a plurality of electrical conductors extending through the cable, a plurality of leads, and a plurality of pin connectors.

5. The electrophysiology catheter system of claim 4 wherein each pin connector comprises a metal pin having a generally uniform outer diameter, and wherein the retractable insulative sheath comprises an insulating lube having a greater diameter than the diameter of the metal pin coaxially disposed about the metal pin and movable from the first position that covers the metal pin and the pan of the nonconducting tip protector to the second position that exposes at least a portion of the metal pin, wherein the insulating tube is biased to the first position.

6. A switch box and cable system for use with a medical device, comprising a) a switch box having at least one receptor and configured to form electrical connections between the receptors and therapeutic and diagnostic electronic components; and b) a cable for connecting the therapeutic and diagnostic electronic components and the switch box, with a distal end having a modular plug configured to mate with and provide electrical connection to the electrophysiology catheter, and a proximal end having at least one lead, the at least one lead being terminated by a pin connector configured to mate with the switch box receptor and having a housing with an opening and a lip, a retractable insulating tube with a flange configured to intercept the housing lip, a metal pin, and a nonconductive tip member on the metal pin, the retractable insulating tube being moveable from a first position that covers the metal pin and a part of the nonconducting tip member which is less than the entire length of the nonconducting tip member to a second position that exposes at least a portion of the metal pin.

7. The system of claim 6, wherein the switch box receptors have an aperture with a diameter larger than the diameter of the metal pin and smaller than the diameter of the insulating tube so that inserting the pin connector into the receptor causes the insulating tube to move to the second position, exposing a portion of the metal pin.

8. An improved method of performing a medical procedure using an electrophysiology device, which minimizes the potential for an electrode on the device to accidentally become electrically energized, comprising a) providing an electrophysiology system comprising an elongated electrophysiology device having a proximal end and a distal end, at least one electrode disposed about the distal end of the device, and a modular plug at the proximal end of the device having an electrical connection with the at least one electrode;

a cable with at least one electrical conductor extending through the cable, a distal end having a modular plug configured to mate with and provide electrical connection to the electrophysiology device, and a proximal end having at least one lead, the at least one lead being terminated by a pin connector having a housing with al opening, a conducting pin extending from the housing opening, and a displaceable insulative sheath in surrounding relation to the conducting pin; and an electronic interface having at least one receptor configured to mate with the pin connector, and having a recess configured to accommodate an outer diameter of the pin connector housing;

b) inserting at least a section of the pin in the receptor and thereby at least in pan displacing the sheath so that the pin is in electrically conductive contact with the interface, and inserting the pin connector housing in the recess; and c) insulating the pin from electrical contact outside of the receptor by extending the sheath over an electrically conductive portion of the pin when the portion of the pin is outside of the receptor.

9. A switch box and cable system for use with a medical device, comprising a) a switch box having at least one receptor having a socket and a recess, and configured to form an electrical connection between the at least one receptor and the medical device; and b) a cable for connecting the medical device and the switch box, with a distal end having a modular plug configured to mate with and provide electrical connection to the medical device, and a proximal end having at least one lead, the at least one lead being terminated by a pin connector configured to mate with the switch box receptor, the pin connector having a housing with an opening, a metal pin extending from the housing opening, and a retractable insulating tube, the recess being configured to accommodate an outer diameter of the pin connector housing.

* * * * *

UNITED STATES PATENT AND TRADEMARK OFFICE
CERTIFICATE OF CORRECTION

PATENT NO.   : 6,167,291
DATED        : December 26, 2000
INVENTOR(S)  : Victor J. Barajas, Duane Dickens Page 1 of 1

It is certified that error appears in the above-identified patent and that said Letters Patent is hereby corrected as shown below:

Column 5,
Line 31, change "leas" to -- least --.
Line 40, change "lube" to -- tube --.
Line 43, change "pan" to -- part --.

Column 6,
Line 28, change "al" to -- an --.
Line 37, change "pan" to -- part --.

Signed and Sealed this

Eleventh Day of September, 2001

Attest:

NICHOLAS P. GODICI
*Acting Director of the United States Patent and Trademark Office*

*Attesting Officer*